United States Patent [19]

Brossi et al.

[11] Patent Number: 5,378,723
[45] Date of Patent: Jan. 3, 1995

[54] CARBAMATE ANALOGS OF THIAPHYSOVENINE AND METHOD FOR INHIBITING CHOLINESTERASES

[75] Inventors: Arnold Brossi, Bethesda; Xiao-shu He, Rockville; Nigel H. Greig, Silver Spring, all of Md.

[73] Assignee: The United States of America as represented by the Secretary of the Dept. of Health and Human Services, Washington, D.C.

[21] Appl. No.: 182,301

[22] Filed: Jan. 18, 1994

Related U.S. Application Data

[63] Continuation of Ser. No. 845,081, Mar. 3, 1992, abandoned, which is a continuation-in-part of Ser. No. 765,766, Sep. 26, 1991, abandoned.

[51] Int. Cl.[6] ............ A61K 31/40; C07D 487/00
[52] U.S. Cl. .................... 514/411; 548/430
[58] Field of Search ............... 548/430; 514/411

[56] References Cited

U.S. PATENT DOCUMENTS 3,133,930  5/1961  Werner et al. ............ 548/430
4,900,748  2/1990  Brossi et al. ............ 514/411

OTHER PUBLICATIONS

Burger, Medicinal Chemistry, 2d Ed., pp. 72–88 (1960).
Qian–Sheng Yu et al, Journal of Medical Chemistry, vol. 31, No. 12, Dec. 1988, pp. 2297–2300.
John R. Atack et al, The Journal of Pharmacology and Experimental Therapeutics, vol. 249, No. 1, Jan. 10, 1989, pp. 194–202.
Beilstein, Ed. II, vol. 23, 1954, p. 333.
The Merck Index, 8th. Ed. (1968), p. 829.
Yu et al., Efficant Synthesis, Anticholinesterase Activity and Analgesic Properties of (−), (+)-Physovenine, Carbamate Analogs of (−)-Physovenine and Thiaphysovenine, (Poster Presentation) Shanghai Institute of Org. of Organic Chemistry, Chinese Academy of Sciences, Shangai 20032, China, p. 203, (Oct. 25, 1991).
Brossi et al., Journal of Natural Products, vol. 48, No. 6, pp. 878–893 (Nov.–Dec. 1985).
Qian-Sheng Yu et al, Heterocycles, vol. 26, No. 5, pp. 1271–1275 (1987).
J. Am. Chem. Soc (57) p. 563 (1935).

*Primary Examiner*—Joseph Paul Brust
*Assistant Examiner*—Mary Susan H. Gabilan
*Attorney, Agent, or Firm*—Lowe, Price, LeBlanc & Becker

[57] ABSTRACT

Substituted carbamates of tricyclic compounds which have a cyclic sulfer atom, provide highly potent and selective cholinergic agonist and blocking activity are useful as pharmaceutical agents. Cholinergic disease are treated with these compounds such as glaucoma, Myasthenia Gravis, Alzheimer's disease. Methods for inhibiting esterases, acetylcholinesterase and butyrylcholinesterase are also provided.

14 Claims, 2 Drawing Sheets

CARBAMATE ANALOGS OF THIAPHYSOVENINE AND METHOD FOR INHIBITING CHOLINESTERASES

This application is a continuation of application Ser. No. 07/845,081 filed Mar. 3, 1992, now abandoned which is a continuation-in-part of U.S. patent application Ser. No. 07/765,766, filed Sep. 26, 1991, now abandoned.

TECHNICAL FIELD

The present invention relates to inhibitors of cholinesterases, pharmaceutical compositions and method of use thereof. More particalar, the invention relates to thiaphysovenine and carbamate analogs and a method of using these potent inhibitors of cholinesterases.

BACKGROUND ART

Physostigmine, also called eserine, and particular derivatives of physostigmine are anticholinesterase inhibitors which are well known. Such well known compounds are also useful in the treatment of glaucoma, Myasthenia Gravis, Alzheimer's disease and as antidotes against poisoning with organophosphates.

It has been discovered that the natural isomer of physostigmine has blocking properties as well as agonist properties at the neuromuscular AChR. By contrast (+)-physostigmine shows only negligible inhibition of cholinesterase (ChE). See Brossi et al., FEBS Lett., Vol. 201, pages 190–192 (1986).

Even though (+)-physostigmine has only negligible ChE inhibitory activity, it is as effective as a protective pretreatment drug against multiple lethal doses of satin, see Albuquerque et al, Fundam. Appl. Caltoxicol., Vol. 5, pages 182–203 (1985). The observed beneficial protection appears to be due to direct interactions of the carbamates with the postsynaptic nicotinic AChR. The protective effectiveness of the carbamates against organophosphates appears to be related to the direct ability of the carbamates to decrease the hyperactivation caused by accumulation of the neurotransmitter.

The above information, available due to the research in this field, is important in the evaluation of potential new pharmacological agents for treating cholinergic disorders, for example, Myasthenia Gravis and Alzheimer's disease. Potential agents can be evaluated for potency in vitro by testing the agents against electric eel acetylcholinesterase (AChE) and human plasma butyrylcholinesterase (BChE).

Of the two enzymes known to hydrolyze acetylcholine (ACh) in vivo, AChE, which is found in red blood cells, in the brain and in nerve tissues, seems to be more specific than BChE which is found in serum, pancreas and in the liver. It, however, has not previously been shown in the art that compounds which selectively inhibit one of the two enzymes more than the other would offer a medical advantage. The natural alkaloid (−)-physostigmine, its potential metabolite (−)-(N1)-norphysostigmine, and the natural alkaloid physovenine which are used as biological standards in this art area, inhibit AChE and BChE in vitro similarly at similar concentrations.

Accordingly, there is need in the art for highly selective agents active against one of AChE and BChE while not being potent against the other so as to lead to better treatment of a particular cholinergic disorder and minimize negative side effects. Such compounds would be of great medical importance in the treatment of cholinergic disorders.

SUMMARY OF THE INVENTION

It is an object of the present invention to provide highly potent and selective cholinergic agonist and blocking compounds.

It is a further object of the present invention to provide improvements in therapy relative to cholinergic diseases such as glaucoma, Myasthenia Gravis, Alzheimer's disease, and organophosphate poisoning.

It is a still further object of the present invention to provide compounds with selective acetylcholinesterase and butyrylcholinesterase activity.

It is an even further object of the present invention to provide (3aS-cis) isomer compounds with absolute configuration identical to that of natural physostigmine, which is a compound of the formula

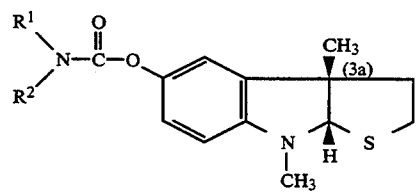

wherein $R^1$ is H or a linear or branched chain $C_1$–$C_{10}$ alkyl group; and $R^2$ is selected from the group consisting of
wherein $R^3$ and $R^4$ are independently selected from the group consisting of H and a linear or branched chain $C_1$–$C_{10}$ - alkyl group;
and with the proviso that when one of $R^1$ or $R^2$ is a H or a methyl group, the other of $R^1$ or $R^2$ is not H; including optical isomers.

DESCRIPTION OF PREFERRED EMBODIMENTS

Figure 1:
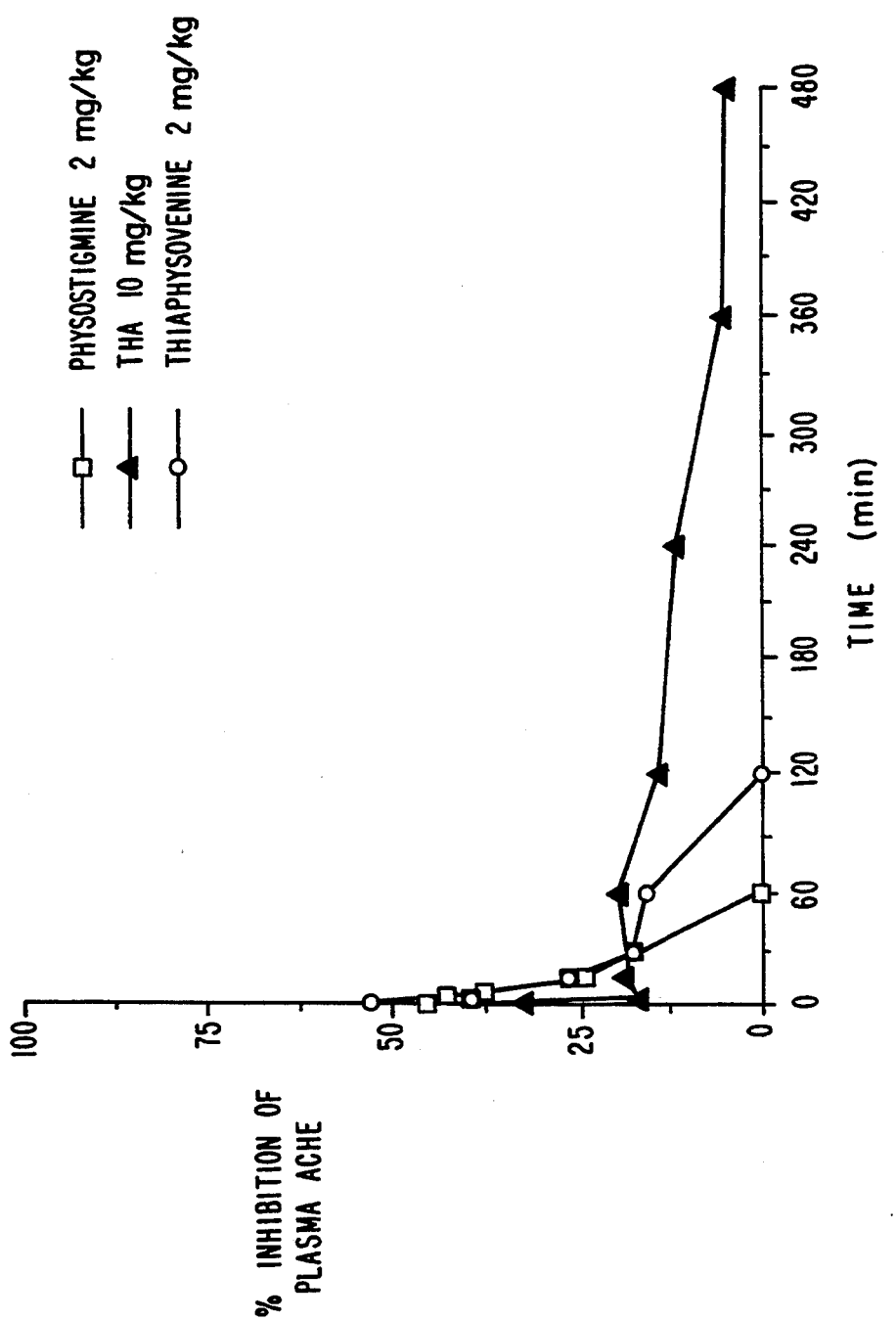
FIG. 1 illustrates the in vivo inhibiton rates and duration of activity for inhibiting the enzyme acetylcholinesterase (AChE) by Tactine (THA), (−)-Physostigmine, and (−)-Thiaphysovenine.

In accordance with this invention there are disclosed compounds of the formula I

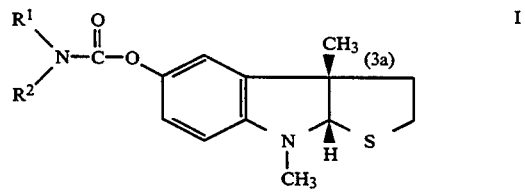

wherein $R^1$ is H or a linear or branched chain $C_1$–$C_{10}$ alkyl group; and $R^2$ is selected from the group consisting of
a linear or branched chain —$C_1$–$C_{10}$ alkyl group, or

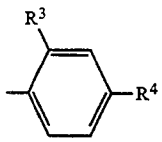

wherein $R^3$ and $R^4$ are independently selected from the group consisting of H and a linear or branched chain $C_1$-$C_{10}$ - alkyl group;
and with the proviso that when one of $R^1$ or $R^2$ is a H or a methyl group, the other of $R^1$ or $R^2$ is not H; including optical isomers.
Preferred are compounds wherein
$R^1$ is H and $R^2$ is $C_4$-$C_{10}$ alkyl;
$R^1$ and $R^2$ are independently $C_1$ —$C_{10}$ alkyl; or
$R^1$ is H and $R^2$ is a group of the formula

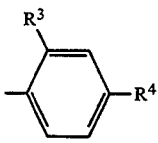

wherein
$R^3$ and $R^4$ are both H or a —$CH_3$ group;
$R^3$ is selected from the group consisting of a methyl, ethyl, or isopropyl group and $R^4$ is H; or
$R^3$ is H and $R^4$ is an isopropyl group.and $R^2$ is a structure of the formula
wherein
$R^3$ is independently H or a —$C_1$—$C_5$-alkyl group and $R^4$ is independently H or a —$C_1$—$C_5$-alkyl group.
Even more preferred are compounds wherein $R^3$ is selected from the group of radicals consisting of H, —$CH_3$, —$CH_2$—$CH_3$, —$CH_2$—$CH_2$—$CH3$, and —$CH(-CH_3)_2$, and $R^4$ is H, —$CH_3$, or —$CH(-CH_3)_2$.

The above compounds are thiaphysovenol carbamic acid derivatives having high potency in the inhibition of acetylcholinesterase and butyrylcholinesterase. Some of the carbamates were more specific for AChE whereas others were more highly specific for BChE.

Other cholinesterase inhibitors are known in the prior art. Physostigmine and physovenine are optically active alkaloids with a (3aS)-absolute configuration at the chiral carbon atom C(3a). Both of these compounds are potent inhibitors of cholinesterases in vitro and in vivo, blocking the conversion of acetylcholine into choline reversibly. Physostigmine has been found to have useful medical applications in disorders which result to a malfunction of this process.

Surprisingly, the thiaphysovenol carbamates according to the present invention have shown high potency. Thus, carbamates with longer aliphatic side chains are long acting and appear to be less toxic than carbamate analogs of physovenine and physostigmine. Accordingly, the present compounds represent a significant advancement in the prior art.

Compositions within the scope of the invention include compositions wherein the active ingredient is contained in an effective amount to achieve its intended purpose. The compounds can be administered in any pharmaceutically acceptable amount, for example, in amounts ranging from 0.001 gram to about 1 gram per kilogram of body weight. Based on the information which is presented herein, the determination of effective amounts is well within the skill of the ordinary practitioner in the art. The compounds are generally useed in pharmaceutical compositions (wt %) containing the active ingredient with a carrier or vehicle in the composition in an amount of about 0.1 to 99 wt % and preferably about 25-85 wt %.

Either fluid or solid unit dosage forins can be readily prepared for oral administration. For example, the compounds of Formula I can be admixed with conventional ingredients such as dicalcium phosphate, magnesium aluminum silicate, magnesium stearate, calcium sulfate, starch, talc, lactose, acacia, methyl cellulose and functionally similar materials as pharmaceutical excipients or carriers. A sustained release formulation may optionally be used. In older or incoherent patients sustained release formulations may even be preferred. Capsules may be formulated by mixing the compound with a pharmaceutical diluent which is inert and inserting this mixture into a hard gelatin capsule having the appropriate size. If soft capsules are desired, a slurry of the compound with an acceptable vegetable, light petroleum or other inert oil can be encapsulated by forming into a gelatin capsule.

Suspensions, syrups and elixirs may be used for oral administration of fluid unit dosage forms. A fluid preparation including oil may be used for oil soluble forms. A vegetable oil such as corn oil, peanut oil or safflower oil, for example, together with flavoring agents, sweeteners and any preservatives produces an acceptable fluid preparation. A surfactant may be added to water to form a syrup for fluid unit dosages. Hydro-alcoholic pharmaceutical preparations may be used having an acceptable sweetener, such as sugar, saccharin or a biological sweetener and a flavoring agent in the form of an elixir.

Pharmaceutical compositions for parenteral and suppository administration can also be obtained using techniques standard in the art.

Preferred uses of the compounds according to the invention are as pharmaceutical agents suitable for oral administration. Another preferred use of the compounds is in transdermal parenteral formulations, which are particularly useful in treating cholinergic disorders such as glaucoma, Myasthenia Gravis, Alzheimer's disease, and organophosphate poisoning. Accordingly, compositions suitable for administration to these areas are particularly included within the invention. The above parenteral solutions or suspensions may be administered transdermally and delivered with a skin patch. If desired they may be given by injection in an appropriate vehicle such as sesame oil.

Accordingly, incorporation of the active compounds and a slow release matrix may be implemented for administering transdermally. The compounds may be administered transdermally in amounts of about 0.01 to 99% of the composition and preferably about 25 to 85 wt % of the active ingredient in the vehicle or carrier.

Transdermal therapeutic systems are self-contained dosage forms that, when applied to intact skin, deliver drug(s) at a controlled rate to the systemic circulation. Advantages of using the transdermal routing include: enhanced therapeutic efficacy, reduction in the frequency of dosing, reduction of side effects due to optimization of blood-concentration vs. time profile, increased patient compliance due to elimination of multiple dosing schedules, bypassing the hepatic "first pass" metabolism, avoiding gastro-intestinal incompatibilities and providing a predictable and extendable duration of activity. However, the main function of the skin is to act as a barrier to entering compounds. As a consequence, transdermal therapy has been preferred for a limited number of drugs that possess the desirable physiochemical properties for diffusion across the skin barrier. One effective method of overcoming the barrier function of the skin is to include a penetration enhancer in the formulation of the transdermal therapeutic system.

The penetration enhancer is a chemical compound that, when included in a formulation, temporarily increases the permeability of the skin to a drug line allowing more of the drug to be absorbed in a shorter period of time. Several different types of penetration enhancers have been reported such as dimethylsulfoxide, n-decyl-methylsulfoxide, N,N-dimethylacetamide N,N-dimethylformamide, 1-dodecylazacycloheptane-2-one (Azone), propylene glycol, ethanol, pyrrolidones such as N-methyl-2-pyrrolidone (NMP) and surfactants.

The above compounds can be present in the reservoir alone or in combination with pharmaceutical carriers. The pharmaceutical carriers acceptable for the purposes of this invention are the known art carriers that do not adversely effect the drug, the host, or the material comprising the drug delivery device. Suitable pharmaceutical carriers include sterile water, saline, dextrose, dextrose in water or saline; condensation products of castor oil and ethylene oxide combining about 30 to 35 moles of ethylene oxide per mole of castor oil, liquid acid, lower alkanols, oils such as corn oil, peanut oil, sesame oil and the like, with emulsifiers such as mono-or di-glyceride of a fatty acid; or a phosphatide, e.g., lecithin, and the like; glycols, polyalkylene glycols, aqueous media in the presence of a suspending agent, for example, sodium carboxymethyl cellulose, sodium alginate, poly(vinylpyrrolidone), and the like, alone, or with suitable dispensing agents such as lecithin, polyoxyethylene stearate, and the like. The carrier may also contain adjuvants such as preserving agents, stabilizing agents, wetting agents, emulsifying agents and the like together with penetration enhancer and the compounds of this invention.

The effective dose for mammals may vary due to such factors as age, weight, activity level or condition of the subject being treated. Typically, an effective dosage of a compound according to the present invention is about 1 to 800 milligrams when administered by either oral or rectal dose from 1 to 3 times daily. This is about 0.002 to about 50 milligrams per kilogram of the subject's weight administered per day. Preferably about 10 to about 300 milligrams are administered orally or rectally 1 to 3 times a day for an adult human. The required dose is considerably less when achninistered parenterally. Preferably about 0.01 to about 150 milligrams may be administered intramuscularly or transdermally, one or two times a day for an adult human.

Compounds of the present invention may be administered topically in amounts of about 0.01 to about 99 wt % of the composition, and preferably about 25 to 85 wt %. The present compounds are also useful in a method for treating cholinergic disorders such as glaucoma, Myasthenia Gravis, Alzheimer's disease, and as an antidote against poisoning with organo phosphates. The method according to the invention comprises administering an effective amount of a compound according to the invention or an effective amount of a pharmaceutical composition according to the invention to a mammal in need of such treatment.

Surprisingly, the compounds according to the invention have shown selective cholinergic agonist and blocking activity. Of the two enzymes known to hydrolyze acetylcholine in vivo, acetylcholinesterase (AChE) which is found in red blood cells, in the brain, and in nerve tissues, seems to be more specific then butyrylcholinesterase (BChE) which is found in serum, pancreas and in the liver. It, however, was never shown that compounds which selectively inhibit one of the two enzymes more than the other, would offer a medical advantage.

The present invention relates to selective inhibition as follows: The natural alkaloid (−)-physostigmine, its potential metabolite (−)-(N1)-norphysostigmine and the natural alkaloid physovenine which were used as biological standards in the inhibited AChE and BChE in vitro similarly at similar concentrations.

Below are three sections illustrating compounds.

The first section (COMPARATIVE) shows standard compounds (A, B, and C), whose biological activity is used to compare with the compounds according to the present invention.

The second section (SCHEME 1) is a flow chart showing a general reaction which produces compounds according to the present invention and avoid separation of isomers by preserving the (3aS-cis)-absolute structure.

The third section (SCHEME 2) is a flow chart showing a general reaction scheme for a complete synthesis for producing compounds according to the present invention.

COMPARATIVE COMPOUNDS

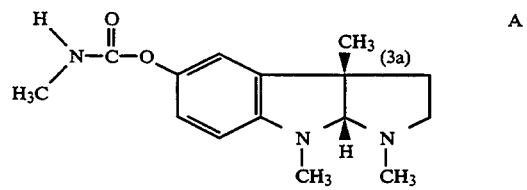

(−)-PHYSOSTIGMINE

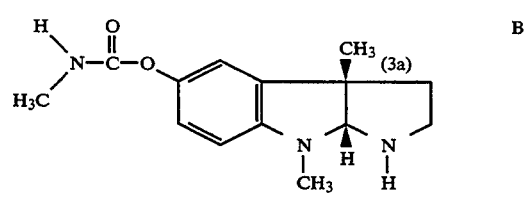

(−)-N(1)-NORPHYSOSTIGMINE

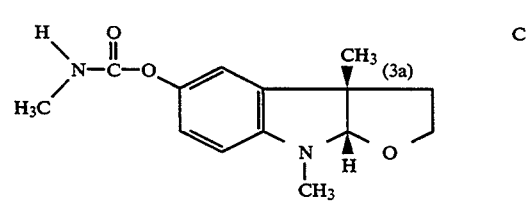

(−)-PHYSOVENINE

SCHEME 1

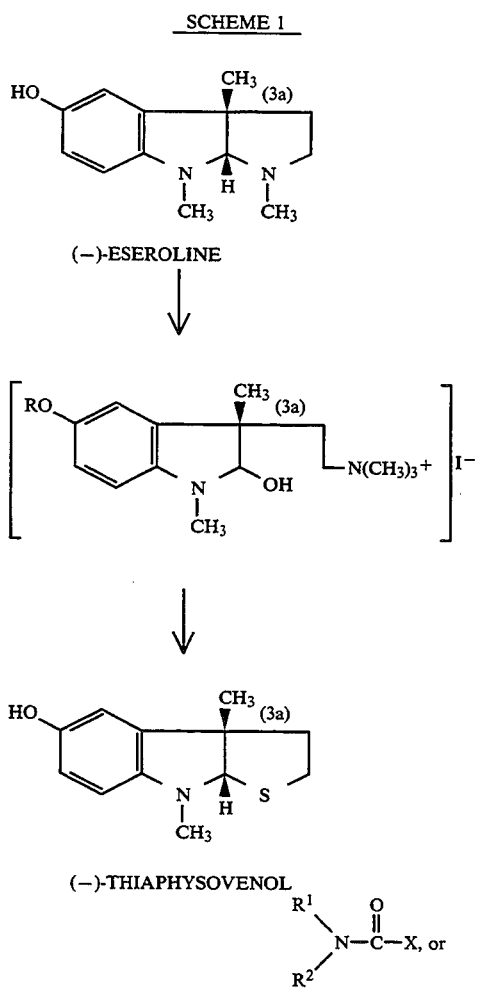

(−)-ESEROLINE (−)-THIAPHYSOVENOL

SCHEME 2

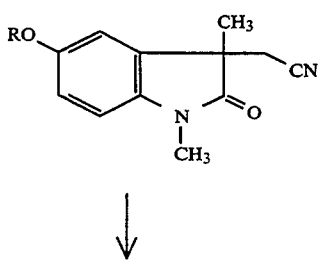

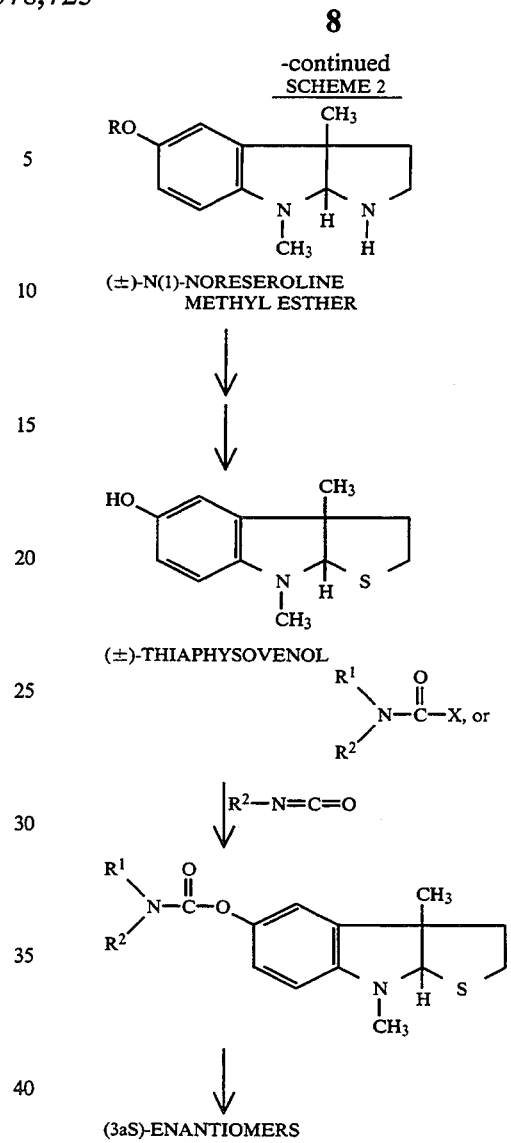

(±)-N(1)-NORESEROLINE METHYL ESTER (±)-THIAPHYSOVENOL (3aS)-ENANTIOMERS

The thiaphysovenol carbamates according to the invention are produced by the following general procedure according to reaction Scheme 1, which is illustrated above.

The starting material in the reaction Scheme 1, (−)-eseroline, is obtained form natural (−)-physostigmine of the (3aS-cis)-absolute configuration by the procedure described by Yu et al. (Heterocycles, 26, page 1271 (1987)). This (−)-eseroline is then subjected to a Hofmann degradation using an alkyl halide, a dialkyl halide, a dialkyl sulfate, a benzyl halide, or the like. Preferred Hofmann reagents are methyl bromide, methyl iodide and benzyl bromide. This reaction affords a carbinolamine, which on reaction, for example, with methyl iodide yields a quaternary salt as an intermediate in the reaction shown in Scheme 1. In this intermediate, the phenolic group of the first reaction product in Scheme 1 has also been converted to an ether, e.g., a methyl ether. (In the intermediates of reaction Schemes 1 and 2, R is used to represent the ether substituent group, e.g., a methyl group.)

This second structure intermediate of reaction scheme 1 is treated with the nucleophile —SH (e.g., sodium hydrogen sulfide) in water which results in the formation of the thienoindole ring system and provides a crucial intermediate in the synthesis of thiaphysovenines. It ((−)-thiaphysovenol methyl ether) is a crystalline solid having a high negative specific rotation. Specifically, for example, a substitution reaction with 7 N sodium mercaptide results in ring closure and leads to a 50–60% yield of crystalline thioether, which is fully characterized by spectral data. The methyl ether portion of the tricyclic structure is reacted to cleave the methyl ether group and convert the phenol into thiaphysovenol carbamates. The same reaction also can be applied to other ethers of thiaphysovenol, such as the ethyl ether or the benzyl ether. Preferred reagents for the cleavage are Lewis acids such as $AlCl_3$ or $BBr_3$. These Lewis acids also cleave other aromatic ethers such as ethyl ethers or benzyl ethers, which may be preferred over the methyl ether. The (−)-thiaphysovenol intermediate structure is the third structure shown in reaction Scheme 1.

Further reaction of the thiaphysovenol in Scheme 1 with an isocyanate ($R^2$—N=C=O) or a disub-stituted-carbamoyl halide (($R^1$, $R^2$)=N—C (=O)—X, with X representing a halide leaving group), by standard protocol (see for example, Yu et al., Heterocycles, 27, page 745 (1988), results in carbamates according to the fourth structure shown in reaction Scheme 1.

As is apparent from reaction Scheme 1, the absolute (3aS-cis) configuration present in (−)-eseroline is preserved in the final thiaphysovenol carbamates.

Accordingly, the present invention includes a process for producing compounds by using a process according to reaction Scheme 1. This invention process is described as follows:

A process for preparing a compound according to the present invention as set forth above which avoids the separation of isomers by preserving the (3aS-cis)-absolute configuration throughout the synthetic procedure, which process comprises (a) subjecting (−)-eseroline, having the (3aS-cis)-absolute configuration

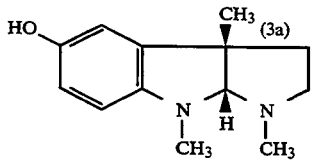

to Hofmann degradation using an alkyl halide, a dialkyl halide, a dialkyl sulfate, a benzyl halide, or the like, which by an elimination reaction yields a bicyclic carbinolamine, which is reacted with the alkyl halide, dialkyl halide, dialkyl sulfate, or the like to yield the quaternary salt having the following formula

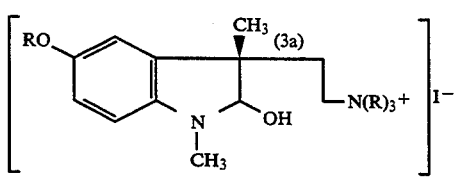

wherein R is an alkyl or benzyl group,
(b) treating the quaternary ammonium salt of step (a) with sodium hydrogen sulfide in water which results in ring closure and the formation of the thienoindole ring system to provide a compound of the following formula

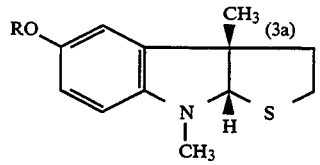

(c) treating the R ether intermediate of step (b) with a Lewis acid to cleave the R ether group to yield a phenol intermediate compound named (−)-thiaphysovenol having the following formula

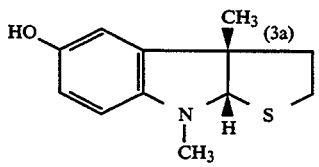

(d) reacting the (−)-thiaphysovenol of step (c) with a compound of the formula

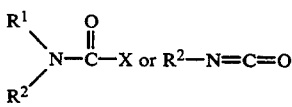

wherein X is a leaving group to provide a thiaphysovenol carbamate compound according to the present invention having the absolute (3aS-cis) configuration.

A second route for producing the compounds according to the present invention is a total synthetic procedure as shown by reaction Scheme 2, set forth above.

The first structure in reaction Scheme 2 is a bicyclic nitrile compound whose phenolic group on the benzo portion has been etherified (Julian et al., J.A.C.S., 57, page 563 (1935); and Schonenberger et al., Helv. Chim. Acta., 69, page 1486 (1986)). This first structure is reacted by published protocol (Yu et al., Heterocycles, 27, page 1709 (1988)) to afford a racemic N(1)-noreseroline ether, e.g., a methyl ether in the second sturucture shown in reaction Scheme 2. For example, this racemic N(1)-noreseroline methyl ether can be prepared from the nitrile by reacting it with lithiumalumium hydride, diisobutyl-aluminum hydride (DIBAH), or a similar reducing agent, in tetrahydrofuran.

The second structure (racemic N(1)-noreseroline) shown in reaction Scheme 2, is then subjected to ether cleavage and reacting the phenol with isocyanates or disubstituted carbamoyl halides.

First racemic N(1)-noreseroline methyl ether of reaction Scheme 2 is subjected to Hofmann degradation and reaction with methyl iodide as in reaction Scheme 1, to yield a racemic quaternary ammonium salt. This salt corresponds to the second structure shown in reaction Scheme 1, but it is optically inactive. This salt is a mixture of the compound shown in Scheme 1 with the (3aS)-absolute structure and its enantiomer (optical isomer).

The next step follows protocol used in the series of the optically active (3aS)-isomers shown in Scheme 1: reaction of the reacemic quaternary ammonium salt with the nucleophile SH— (sodium hydrogen sulfide) in water results in the formation of racemic thiaphysovenol methyl ether, and the corresponding phenol (racemic thiaphysovenol) is obtained upon treatment with Lewis acid, preferentilly carried out in a solvent such as methylene chloride or carbon tetrachloride. Reaction of this phenol with isocyanates or disubstituted carbamoyl chlorides affords the desired racemic carbamate esters. They are purified by chromatography.

The racemic esters can be resolved into optical isomers on chiral choluns, or by chromatography on cellulose triacetate as described in the literature for racemic physovenine derivatives (see, for example, Yu et al., Helv. Chim. Acta, 74, page 761 (1991)).

The reaction step of both reaction Schemes 1 and 2 that reacts the quaternary ammonium salt with the —SH nucleophile (e.g., sodium hydrogen sulfide) to yield the thienoindoline structure is an important novel reaction step. This step is essential for preparing the carbamates covered by the present application. This procedure has also not previously been reported in the lite rature. The quaternary ammonium carbinolamines can be separated or reacted with an —SH nucleophile to yield a thienoindoline structure.

Although conversion of pyrrolindoles into furanoindoles to produce physovenines was executed without isolation of the intermediate quaternary carbinolamines, it was shown that they are indeed the ultimate precursors in this reaction (Dale et al., J. Pharm. Pharmacol. 22, page 889 (1970)).

As described above in discussing reaction Schemes 1 and 2, the general procedures reported in the literature for making carbamates of the physovenine series and the physostigmine series can be followed to produce the carbamates according to the present invention. For example, in reaction Schemes 1 and 2, the N-disubstituted carbamates were prepared from (—)-thiaphysovenol or its racemic equivalents by reaction with dimethyl carbamoyl chloride, as reported in the physostigmine series. Also, the NH-carbamates are obtained with (—)-thiaphysovenol or its racemic equivalents by reaction with substituted isocyanates.

Accordingly, the present invention also includes a process for making the compounds of the racemic series according to the present invention using the reaction Scheme 2 as described above, followed by resolution of the racemic mixture. The procedures are as follows.

A total synthetic process for producing compounds according to present invention first produces a racemic carbamate derivative followed by separation of the compounds according to the present invention from the racemate, which process comprises:

(a) reaction of a ether substituted bicyclic nitrile compound, wherein R represents the substituent attached to the oxygen atom to form the ether group (R is methyl, for example, but it may be replaced by another alkyl group such as ethyl, which was used by Julians total synthesis (Julian et al., J.A.C.S. 57, page 563 (1935)) or benzyl, wherein the ether substituted nitrile compound has the following formula

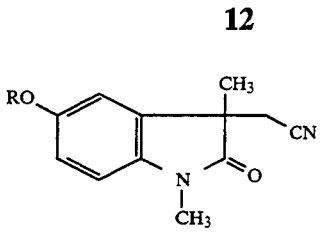

wherein R is a removable alkyl or benzyl phenol protecting group, with lithium aluminum hydride, DIBAH, or the like in an inert solvent to produce a racemic N(1)-noreseroline methyl ether compound having the following formula

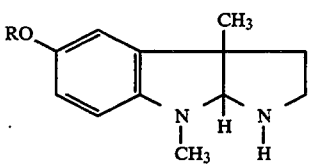

(b) the racemic N(1)-noreseroline R ether, which is produced by step (a) is then subjected to Hofmann degradation using an alkyl halide, a dialkyl halide, a dialkyl sulfate, a benzyl halide, or the like, which by an elimination reaction yields a bicyclic carbinolamine, which is reacted with the alkyl halide, dialkyl halide, dialkyl sulfate, benzyl halide or the like to yield the racemic quaternary salt having the following formula

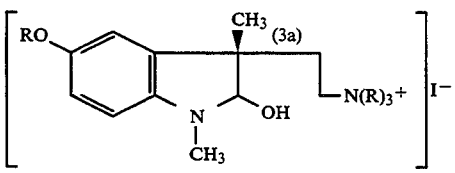

(c) treating the quaternary ammonium salt of step (b) with sodium hydrogen sulfide in water which results in ring closure and the formation of the thienoindole ring system to provide a racemic compound of the following formula

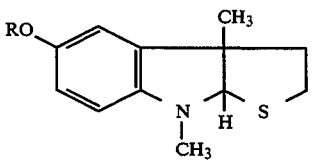

(d) the R ether intermediate of step (c) is then
  (i) treated to remove the R ether group and yield a phenolic intermediate of formula

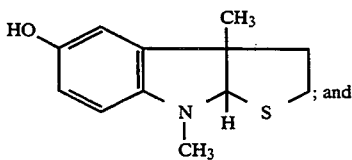

(ii) the phenolic intermediate compound of step (d:i) is then reacted with a compound of the formula

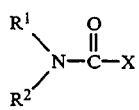

wherein X is a leaving group; or
(iii) the phenol of step (d:i) is reacted with a substituted isocyanate compound of the formula

in the presence of an alkaline metal catalyst in an inert solvent to provide a racemic thiaphysovenol carbamate compound of formula

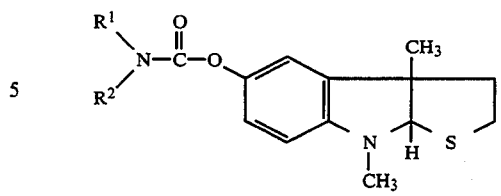

wherein $R^1$ and $R^2$ are defined as above; and (e) separating the racemic mixture to yield a thiaphysovenine compound having the absolute (3aS-cis) configuration.

Compounds according to the invention are listed in Table I.

TABLE I

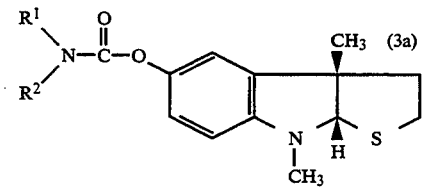

| COMP. | R₂ | R¹ | R₃ | R₄ |
|---|---|---|---|---|
| 1 | —CH₂—(CH₂)₂—CH₃ | —H | — | — |
| 2 | —CH₂—(CH₂)₅—CH₃ | —H | — | — |
| 3 | 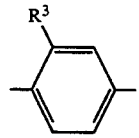 | —H | —H | —H |
| 4 | 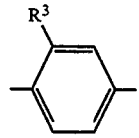 | —H | —CH₃ | —H |
| 5 | 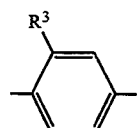 | —H | —CH₂—CH₃ | —H |
| 6 | 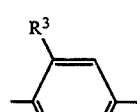 | —H | —CH(—CH₃)₂ | —H |
| 7 | 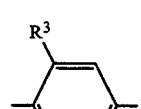 | —H | —H | —CH(—CH₃)₂ |
| 8 | 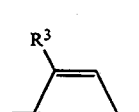 | —H | —CH₃ | —CH₃ |
| 9 | —CH₃ | —CH₃ | — | — |

EXPERIMENTAL DATA

M.p. (uncorrected): Fisher-Johns apparatus; $^1$H-NMR spectra (300 MHz): Varian XL-300 spectrometer, δ in ppm rel. to TMS (=0.0 ppm) as internal standard; Mass spectra for chemical ionization (CI-MS, m/z): Finnigan-1015D mass spectrometer, and for electron impact (EI-MS) and high resolution mass measurement (HRMS): VG-Micro Mass 7070F mass spectrometer; Optical rotation ($[\alpha]_D$): Perkin-Elmer-241 MC automatic polarimeter; silica gel plates were purchased from Analtech Inc., Newark, N.J.; Column chromatology (GHLF): Merck 60 (230–400 mesh); solvent systems used for TLC: (A) $CHCl_3/CH_3OH/NH_4OH=90/9/1$; (B) $CHCl_3/CH_3OH=96/4$.

(−)-Eseroline (the first structure in reaction Scheme 1) is prepared from (−)-physostigmine by a procedure well known in the art as discussed above.

EXPERIMENT 1

(−)-3,3a,8,8a-Tetrahydro-3a,8-dimethyl-2H-thieno[2,3-b]indole-5-ol methyl ether.

(−)-Eseroline (2.66 g, 12.10 mmol) was dissolved in DMSO (150 ml) under $N_2$-atmosphere at R.T. Powdered KOH (2.80 g, 49.9 nunol) was. added. After stirring for 5 minutes at R.T. in $N_2$-atmosphere, $CH_3I$ (3.59 g, 25.3 mmol) was added, and the stirring continued for 1 hour. Then $CH_3I$ (7.3 g, 51.4 mmol) was added and the reaction mixture stirred for another hour. It was washed with $Et_2O$ (50 ml×2) to remove excess $CH_3I$ and some DMSO, and the remaining solution evaporated in vacuo to remove low boiling solvents, then added with 7 N NaHS (115 ml) and refluxed for 2 hours. After cooling, the reaction mixture was extracted with $Et_2O$ (100 ml×3). The combined extracts were washed with 10% citric acid (50 ml×3) and brine (50 ml×2), dried (anh. $Na_2SO_4$) and evaporated in vacuo to give a yellowish oil 2.33 g which was passed through a column chromatography [silica gel, eluted by $CH_2Cl_2/CH_3OH$ (250/1)] to give 1.82 g (63.6%) of the methyl ether as colorless crystals: m.p. 40°–41° C.; CI-MS: MH+ 236; $^1$H-NMR ($CDCl_3$): δ1.45 (s, 3H, C(3a)—$CH_3$), 2.21–2.85 (m, 4H, 2, 3—$CH_2$), 2.79 (s, 3H, N—$CH_3$), 3.78 (s, 3H, O—$CH_3$), 5.10 (s, 1H, C(8a)—H), 6.39 (d, 1H, J=8.2, 7—H), 6.66 (d, 1H, J =2.5, 4—H), 6.70 (dd, 1H, J=2.5, 8.2, 6—H) ppm; $[\alpha]_D$ −246.14° (c 1.33, EtOH).

Anal. Calc. for $C_{13}H_{17}NSO$ (235.341): C 66.34, H 7.28, N. 5.95. S 13.62; Found: C 66.30, H 7.32, N 5.93, S 13.53.

EXPERIMENT 2

Production of Thiaphysovenol from the Methyl Ether Produced in Experiment 1.

(−)-3,3a,8,8a-Tetrahydro-3a,8-dimethyl-2H-thieno[2,3-b]indole-5-ol.

The methyl ether from Experiment 1 (1.87 g. 8 mmol) was dissolved in $CH_2Cl_2$ (80 ml) and then the solution of $BBr_3$ (7 ml) in $CH_2Cl_2$ (30 ml) added dropwise with stirring under $N_2$-atmosphere at R.T. After 2 h, MeOH was added cautiously under cooling (a water bath), and volatile gases released by opening the reaction vessel. The solvent was evaporated in vacuo. The residue was dissolved in $H_2O$ (22 ml), made alkaline by the addition of 10% $NaHCO_3$, and extracted with $Et_2O$ (100 ml×3). The $Et_2O$ phase was washed with brine (30 ml×2), dried (anh. $Na_2SO_4$) and evaporated in vacuo to give a yellowish foam 1.57 g which was subjected to a flash chromatography (silica gel, eluted by $CH_2Cl_2$) to give pink crystals which was triturated in iso-octane to give 1.2 g of thiaphysovenol as off-white crystals (67.9%): m.p. 112°–113° C.; CI-MS: MH+ 222; $^1$H-NMR ($CDCl_3$): δ1.41 (s, 3H, C(3a)—$CH_3$), 2.18–2.81 (m, 4H, 2,3—$CH_2$), 2.75 (s, 3H, N—$CH_3$), 4.28 (s, 1H, exchanges with $D_2O$, O—H), 5.07 (s, 1H, C(8a)—H), 6.30–6.60 (m, 3H Ar-H) ppm; $[\alpha]_D$ −262.92° (c 0.99, EtOH).

Anal. Calc. for $C_{12}H_{15}NSO$ (221.31): C 65.12, H 6.83, N 6.33, S 14.49; Found: C 65.06, H 6.87, N 6.29, S 14.42.

EXPERIMENT 3

Production of Carbamates of Thiaphysovenol, (−)-3, 3a, 8, 8a-tetrahydro-3a, 8-dimethyl-2H-thieno-[2,3-b]indole-5-ol butyl carbamate.

Thiaphysovenol (1 mmol) was dissolved in anhydrous ether (20 ml) and a small piece of sodium (ca. 1 mg) added. After stirring for 5 minutes at R.T. in $N_2$-atmosphere, N-butylisocyanate (1.1 mmol) was added. The reaction mixture was stirred for 20 hours at R.T. under $N_2$-atmosphere, then sodium was removed, the solvent was evaporated in vacuo and the residue was dissolved in EtOAc. The EtOAc phase was washed with 0.1 N NaOH, brine, dried (and. $Na_2SO_4$) and evaporated in vacuo to give pink foam which was subjected to a column chromatography ( silica gel , $CH_2Cl_2/CH_3OH$ ( 250/1 )] to give the butyl carbamate. It was crystallized with EtOAc-hexane to give the butyl carbamate as colorless crystals (47.5%): m.p. 92°–93° C.; CI-MS: MH+ 321; $^1$H-NMR ($CDCl_3$): δ0.95 (t, 3H, J=7.2, chain—$CH_3$), 1.43 (s, 3H, C(3a)—$CH_3$), 1.37–1.57 (m, 4H, chain—$CH_2CH_2$—$CH_3$), 2.18–2.81 (m, 4H, 2, 3—$CH_2$), 2.79 (s, 3H, N(8)—$CH_3$), 3.25 (q, 2H, J=6.8, chain-N—$CH_2$), 4.90 (br, 1H, N—H), 5.07 (s, 1H, C(8a)—H), 6.35–6.85 (m, 3H, Ar—H) ppm; $[\alpha]_D$ −217.97° (c 0.76, EtOH).

Anal. Calc. for $C_{17}H_{24}N_2SO_2$ (320.444): C 63.71, H 7.55, N 8.74, S 10.01; Found: C 63.65, H 7.61, N 8.74, S 10.09.

EXPERIMENT 4

The Production of (−)-3, 3a,8,8a-tetrahydro-3a,8-dimethyl-2H-thieno[2,3-b]indole-5-ol heptylcarbamate from thiaphysovenol.

The same general procedure was followed as in Experiment 3, but N-heptylisocyanate was used as the reactant instead of N-butylisocyanate. It was triturated with hexane to give the heptyl carbamate as colorless crystals (45.1%): m.p. 84° C.; CI-MS: MH+ 363; $^1$H-NMR ($CDCl_3$): δ0.89 ( t, 3H, chain—$CH_3$ ), 1.43 ( s, 3H, C(3a)—$CH_3$), 1.29–1.57 (m, 10H, chain—$CH_2$)$_5$—$CH_3$ ), 2.18–2.82 (m, 4H, 2,3—$CH_2$), 2.79 (s, 3H, N—$CH_3$), 3.22 (q, 2H, J=6.6, chain-N—$CH_2$), 4.93 (s, 1H, N—H) , 5.08 (s, 1H, C(8a)—H), 6.36–6.85 (m, 3H, Ar-H ) ppm; $[\alpha]_D$- 216.36° (c 1.05, $CHCl_3$).

Anal. Calc. for $C_{20}H_{30}N_2SO_2$ ( 362. 524 ): C 66.26 , H 8.34, N 7.73, S 8.84; Found: C 66.37, H 8.35, N 7.75, S 8.93.

EXPERIMENT 5

Production of
(−)-3,3a,8,8a-tetrahydro-3a,8-dimethyl-2H-thieno[2,3-b]indole-5-ol phenylcarbamate from thiaphysovenol.

The same general procedure was followed as in Experiment 3, but N-phenylisocyanate was used as the reactant. The resulting carbamate was crystallized with ether to give the phenyl carbamate as colorless crystals (69.0%): m.p. 175°–176° C.; CI-MS: MH+ 341; $^1$H-NMR (CDCl$_3$); $\delta$1.45 (s, 3H, C(3a)—CH$_3$), 2.81 (s, 3H, N—CH$_3$), 2.15–2.82 (m, 4H, 2, 3—CH$_2$), 5.09 (s, 1H, C(8a)-H), 6.38–6.93 (m, 3H, Ar-H), 7.07–7.45 (m, 5H, Ar-H) ppm; $[\alpha]_D$ −258.76° (c 0.84, CHCl$_3$).

Anal. Calc. for C$_{19}$H$_{20}$N$_2$SO$_2$ (340.434): C 67.03, H 5.92, N 8.23, S 9.42; Found: C 66.94, H 5.95, N 8.26, S 9.48.

EXPERIMENT 6

The production of
(−)-3,3a,8,8a-tetrahydro-3a,8-dimethyl;-2H-thieno[2,3-b]indole-5-ol 2'-methylphenylcarbamate from thiaphysovenol.

The same general procedure was followed as in Experiment 3, but N-(2-methylphenyl)isocyanate was used as the reactant. The resulting carbamate was a colorless foam (66.5%): CI-MS; MH+ 355; $^1$H-NMR (CDCl$_3$): $\delta$1.45 (s, 3H, C(3a)—CH$_3$), 2.32 (s, 3H, chain-2'—CH$_3$), 2.80 (s, 3H, N—CH$_3$), 2.18–2.83 (m, 4H, 2,3—CH$_2$), 5.09(s, 1H, C(8a)—H), 6.38–6.94 (m, 3H, Ar—H), 7.03–7.25 (m, 4H, Ar-H) PPM; $[\alpha]_D$ −148.53° (c 0.68, CHCl$_3$).

Anal. Calc. for C$_{20}$H$_{22}$N$_2$SO$_2$.0.75 H$_2$O (367.979): C 65.28, H 6.44, N 7.61, S 8.71; Found: C 65.66, H 6.20, N 7.57, S 8.68.

EXPERIMENT 7

Production of
(−)-3,3a,8,8a-tetrahydro-3a,8-dimethyl-2H-thieno[2,3-b]indole-5-ol 2'-ethylphenylcarbamate from thiaphysovenol.

The same general procedure was followed as in Experiment 3, but N-(2-ethylphenyl)isocyanate was used as the reactant. It was a colorless foam (70.5%): CIMS: MH+ 369, 222 (100%); $^1$H-NMR (CDCl$_3$); $\delta$1.28 (t, 3H, J=7.57, chain-2'—C—CH$_3$), 1.44 (s, 3H, C(3a) —CH$_3$), 2.15–2.84 (m, 6H, 2,3—CH$_2$ and chain —2'—CH$_2$—CH$_3$), 2.80 (s, 3H, N—CH$_3$), 5.09 (s, 1H, C(8a)—H), 6.38–6.93 (m, 3H, Ar-H), 7.08–7.23 (m, 4H, Ar-H) ppm; $[\alpha]_D$ −237.7° (c 0.27, CHCl$_3$).

Anal. Calc. for C$_{21}$H$_{24}$N$_2$SO$_2$.0.25 H$_2$O (372.989): C 67.62, H 6.62, N 7.51, Found: C 67.59, H 6.60, N 7.52.

EXPERIMENT 8

Production of
(−)-3,3a,8,8a-tetrahydro-3a,8-dimethy-2H-thieno[2,3-b]indole-5-ol 2'-isopropylphenylcarbamate from thiaphysovenol.

The same general procedure was followed as in Experiment 3, but N-(2-isopropylphenyl)isocyanate was used as the reactant. It was a colorless oil (86.5%): CI-MS: MH+ 383, 222 (100%); $^1$H-NMR (CDCl$_3$): $\delta$1.29 (d, 6H, chain-2'—C—(CH$_3$)$_2$), 1.44 (s, 3H, C(3a-)—CH$_3$), 2.20 (m, 1H, chain-2'—CH-Me$_2$), 2.54–2.83 (m, 4H, 2,3—CH$_2$), 2.80 (s, 3H, N—CH$_3$), 5.09 (s, 1H, C(8a)—H), 6.38–6.94 (m, 3H, Ar-H), 7.16–7.31 (m, 4H, Ar-H) ppm; $[\alpha]_D$ −211.22° (c 0.41, CHCl$_3$).

Anal. Calc. for C$_{22}$H$_{26}$N$_2$SO$_2$ (382.514): C 69.07, H 6.85, N 7.33, S 8.38; Found: C 68.93, H 6.90, N 7.26, S 8.28.

EXPERIMENT 9

Production of
(−)-3,3a,8,8a-tetrahydro-3a,8-dimethyl-2H-thieno[2,3-b]indole-5-ol 4'-isopropylphenylcarbamate from thiaphysovenol.

The same general procedure was followed as in Experiment 3, but N-(4-isopropylphenyl)isocyanate was used as the reactant. It was triturated with etherhexane to give the 4'-isopropylphenylcarbamate as colorless crystals (41.7%): m.p. 198°–200° C.; EI-MS: MH+ 221, 161 (100%), 146,128; $^1$H-NMR (CDCl$_3$); $\delta$1.23 (d, 6H, chain-4'—C—(CH$_3$)$_2$), 1.44 (s, 3H, C(3a)—CH$_3$), 2.15–2.93 (m, 5H, 2,3—CH$_2$ and chain-4'—CH—((CH$_3$)$_2$), 2.80 (s, 3H, N—CH$_3$), 5.09 (s, 1H, C(8a-)—H), 6.38–6.92 (m, 3H, Ar-H), 7.17–7.36 (dd, 4H, Ar-H) ppm; $[\alpha]_D$ −221.25° (c 0.65, CHCl$_3$).

Anal. Calc. for C$_{22}$H$_{26}$N$_2$SO$_2$.0.75 H$_2$O (396.029): 66.72, H 7.00, N 7.08, S 8.10; Found: C 66.71, H 6.74, N 7.12, S 8.04.

EXPERIMENT 10

Production of (−)
-3,3a,8,8a-tetrahydro-3a,8-dimethyl-2H-thieno[2,3-b]indole-5-ol 2',4'-dimethylphenylcarbamate from thiaphysovenol.

The same general procedure was followed as in Experiment 3, but N- 2,4-dimethylphenyl)isocyanate was used as the reactant. It was an off-white foam (58.2%): m.p. 51°–53° C.; CI-MS: MH+ $^1$H-NMR (CDCl$_3$): $\delta$1.44 (s, 3H, C(3a)—CH$_3$), 2.29 (d, 6H, chain-2',4'—CH$_3$), 2.15–2.83 (m, 4H, 2,3—CH$_2$), 2.80 (s, 3H, N—CH$_3$), 5.09 (s, 1H, C(8a)—H), 6.38–6.93 (m, 3H, Ar-H), 7.01–7.04, (d, 3H, Ar-H) ppm; $[\alpha]_D$ −193.5° (c 1.18, EtOH)

Anal. Calc. for C$_{21}$H$_{24}$N$_2$SO$_2$ (368.484): C 68.45, H 6.56, N 7.60, S 8.70; Found: C 68.45, H 6.57, N 7.57, S 8.76.

EXPERIMENT 11

Production of
(−)-3,3a,8,8a-tetrahydro-3a,8-dimethyl-2H-thieno[2,3-b]indole-5-ol N,N-dimethylcarbamate.

Freshly prepared thiaphysovenol (350 mg, 1.58 mmol) was dissolved in 5 ml of pyridine, and 860 mg (8 mmol) of N,N-dimethylcarbamoyl chloride added. The reaction mixture was stirred at 50° C. under N$_2$-atmosphere overnight, and after the addition of 0.2 ml of Et$_3$N kept for 3 additional hours at 50° C. The solvent was evaporated in high vacuum to give an orange glasslike compound which was dissolved in EtOAc/H$_2$O (100 ml/50 ml). The EtoAc phase was washed with 2 N HCl, brine, dried (anh. Na$_2$SO$_4$) and evaporated in vacuo to give a colorless oil. The oil was flash chromotographed on a silica gel column [CH$_2$Cl$_2$/CH$_3$OH (250/1)] to give 260 mg of the N,N-dimethylcarbamate as a colorless oil (64.5%) (and 50 mg of starting material, thiaphysovenol): CI-MS: MH+ 293; $^1$H-NMR (CDCl3): $\delta$1.43 (s, 3H, C(3a)—CH$_3$), 2.17–2.77 (m, 4H, 2,3—CH$_2$), 2.79 (s, 3H, N(8)—CH$_3$), 3.03 (d, 6H, N-(CH$_3$)$_2$), 5.07 (s, 1H, C(8a)—H), 6.38–6.84 (m, 3H, Ar-H) ppm; $[\alpha]_D$ −208.11° (c 1.15, EtOH).

Anal. Calc. for $C_{15}H_{20}N_2SO_2$(292.394): C 61.61, H 6.89, N 9.58, S 10.97; Found: C 61.51, H 6.93, N 9.49, S 10.90.

The complete synthetic procedure according to Scheme 2 is indicated by the following experiments.

EXPERIMENT 12

Production of fumarate salt of racemic (±)-O-methyl-N(1)-noreseroline.

To a stirred solution of $LiAlH_4$ in THF (91 ml, 1.0 M solution) was added, dropwise, a solution of nitrile having the formula shown by the first structure of reaction Scheme 2, (10.5 g, 45.6 mmol) in THF (25 ml) at R.T. under $N_2$-atmosphere. The reaction mixture was first stirred at R.T. for 1 hour and then refluxed for an additional one-half hour. After cooling, the reaction mixture was diluted with THF (92 ml), treated with $H_2O$ (3.9 ml), 15% NaOH aqueous solution (3.9 ml) and $H_2O$ (11 ml) in ice bath. It was stirred for 15 minutes, then filtered. The filtrate was evaporated in vacuo to give brown oil, which was dissolved in 2 N HCl. The acidic aqueous solution was washed with $Et_2O$ (50 ml×2), then, adjusted to pH 9 with $K_2CO_3$ and extracted with $Et_2O$ (100 ml×3). The combined extracts were washed with brine (40 ml×2), dried (anh. $Na_2SO_4$) and concentrated to about 50 ml, a saturated EtOH solution of fumaric acid 5.28 g was added. Recrystallization of the salt from EtOH gave the fumarate of (±)-O-Methyl-N(1)-noreseroline (7.6 g, 50%): m.p. 201°–203° C. (d); CI-MS: MH+ 219; $^1$H-NMR ($CDCl_3$); δ 1.42 (s, 3H, C(3a)—$CH_3$), 1.74–3.09 (m, 4H, 2,3—$CH_2$), 2.79 (s, 3H, N(8)—$CH_3$), 3.75 (s, 3H, O—$CH_3$), 4.42 (s, 1H, C(8a-)—H), 6.25–6.68 (m, 3H, Ar-H) ppm.

Anal . Calc . for $C_{13}H_{18}N_2O \cdot C_4H_4O_4$ (334.37 ): C 61.06, H 6.63, N 8.38; Found: C 60.99, H 6.60, N 8.35.

EXPERIMENT 13

Preparation of (±)-3,3a,8,8a-tetrahydro-3a,8-dimethyl-2H-thieno[2,3-b]indole-5-ol methyl ether.

The free base of the (±)-O-methyl-N ( 1 )-noreseroline fumarate from Experiment 12 was obtained by adjusting the pH to 8. The same general procedure as for the Experiment 1 was followed, but using the free base (±)-O-Methyl-N(1)-noreseroline as the starting material instead of (−)-eseroline, and $CH_3I$ was added after instead of before the KOH was added. The procedure results in (±)-3,3a 8 8a-tetrahydro-3a,8-dimethyl-2H-thieno[2,3-b]indole-5-ol methyl ether as a colorless oil (27%). TLC, MS, $^1$H-NMR were identical with the 3aS-cis compound yielded by Experiment 1, above; HRMS M+ (calc. for $C_{13}H_{17}NSO$): 235.1031, M+ (found) 235.1039.

EXPERIMENT 14

Production of (±)-3,3a,8,8a-tetrahydro-3a,8-dimethyl-2H-thieno[2,3-b]indole-5ol ((±)-thiaphysovenol) from the methyl ether.

The methyl ether was demethylated as described in Experiment 2, above. Workup resulted in an oil (66.2%): TLC, MS, $^1$H-NMR were identical with (−)-thiaphysovenol; HRMS M+ (calc. for $C_{12}H_{15}NSO$): 221.0874, M+ (found): 221.0880.

EXPERIMENT 15

Production of (±)-3,3a,8,8a-Tetrahydro-3a,8-dimethyl-2H-thieno [2,3-b]indole-5-ol 2′,4′-dimethylphenylcarbamate from racemic thiaphysovenol.

The same procedure is followed as in Experiment 10, but racemic thiaphysovenol is used as the starting material. Workup yielded a colorless oil (43.8% ). TLC, MS, $^1$H-NMR were identical with the (−)-isomer described in Experiment 10.

Anal. Calc. for $C_{21}H_{24}N_2SO_2$ 0.75 $H_2O$ (381.999): C 66.02, H 6.73, N 7.34, S 8.39; Found: C 66.29, H 6.52, N 7.40, S 8.32.

EXPERIMENT 16

The resolution of (±)-3,3a,8,8a-tetrahydro-3a,8-dimethyl-2H-thieno[2,3-b]indole-5-ol 2′-methylphenylcarbamate.

The optical resolution of the racemic mixture is accomplished by chromatography on cellulose triacetate columns as described for physovenine (Yu et al., Helv. Chim. Acta, 74, page 761 (1991)). Upon resolution the resulting TLC, MS $^1$H-NMR and optical rotation are identical with (−)-3,3a,8,8a-Tetrahydro-3a,8-dimethyl2H-thieno[2,3-b]indole-5-ol 2′-methylphenylcarbamate prepared in Experiment 6, above.

EXPERIMENT 17

Production of (±)-3,3a,8,8a-tetrahydro-3a,8-dimethyl-2H-thieno[2,3-b]indole-5-ol 4′-isopropylphenylcarbamate from racemic thiaphysovenol.

The same procedure was used as in Experiment 9, but racemic thiaphysovenol was used. It was obtained as colorless crystals (from ether-hexane, 78.5%): m.p. 184°–185° C.; CI-MS: MH+ 383, 222 (100%); TLC, $^1$H-NMR were identical with the corresponding optically active compound of Experiment 9.

Anal. Calc. for $C_{22}H_{26}N_2SO_2$ (382.514): C 69.07, H 6.85, N 7.33, S 8.38; Found: C 69.14, H 6.91, N 7.37, S 8.42.

EXPERIMENT 18

Resolution of (±)-3,3a,8,8a-tetrahydro-3a,8-dimethyl-2H-thieno[2,3-b]indole-5-ol 4′-isopropylphenylcarbamate.

The optical resolution of the racemic mixture obtained in experiment 17 is accomplished as described in Experiment 16, above. Upon resolution the resulting TLC, MS, $^1$H-NMR, and optical rotation are identical with (−)-3,3a,8,8a-tetrahydro-3a,8-dimethyl-2H-thieno[2,3-b]indole-5-ol 4′-isopropylphenylcarbamate prepared in Experiment 9, above.

BIOLOGICAL EXPERIMENTAL

In Vitro Assay of Human Anti-AChE and —BChE activity, $IC_{50}$

A classical enzyme inhibition assay was undertaken to quantirate the activity of the control compounds (A, B, and C ) derivatives against AChE and BChE. Anticholinesterase activity was determined against human erythrocyte AChE and plasma BChE in 0.1M $Na_3PO_4$ buffer (pH 8.0 ) , using the spectrophotometric method of Ellman et al . ( Biochem. Pharmacol. 7, page 88, (1961)). Freshly collected blood was centrifuged (6000×g, 10 min, 4 °C.), the plasma was separated and diluted 1: 125 with 0.1 Na$_3$PO$_4$ (pH 7.4). Erythrocytes were washed three times in isotonic saline, lysed by the addition of 9 volumes of Na$_3$PO$_4$ containing 0.5% Triton-X (Sigma Chemical Co., St. Louis, Mo.) (pH 7.4 on ice for 30 min) and diluted with 19 volumes of 0.1M Na$_3$PO$_4$ (pH 7.4), to a final dilution of 1: 200. Acetyl-β-methylthiocholine (0.5 mM) (Sigma) and s-Butyrylthiocholine (0.5 mM) (Sigma) were used as specific substrates for the assay of AChE and BChE, respectively. For each cholinesterase preparation 25 μl of enzyme were added to a final incubation volume of 0.75 ml.

The compounds tested were initially dissolved in Tween 80/EtOH (3:1, V:V, 75 μl total volume), diluted with 0.1 M Na$_3$PO$_4$ (pH 8.0) in half log-intervals to a final concentration range of between $1\times10^{-5}$ M and $3\times10^{-10}$ M, and were preincubated with enzyme (30 min at 21° C.) prior to addition of substrates. The Tween 80/EtOH was diluted in excess of 1:1000 and did not affect either AChE or BChE activity. Following a 25 rain incubation, at 37° C., production of a yellow thionitrobenzoate anion was measured with a spectrophotometer set to 412 nm wavelength. Nonspecific substrate hydrolysis was determined under conditions of complete enzyme inhibition (by addition of physostigmine $1\times10^{-5}$ M), and the associated change in absorbance was subtracted from that observed with the test compounds. Furthermore, the activity of each compound was assessed alongside that of physostigmine, as an external standard, whose activity has been previously reported (See, Yu et al., Helv. Chim. Acta 74, page 761 (1991) and Yu et al., 31, page 2297 (1988)).

The pharmacological activity of each compound was expressed as an IC$_{50}$, which is defined as the concentration, in nanomoles, required to inhibit 50% of the enzyme activity of AChE and BChE, separately. For determination of IC$_{50}$ values, the enzyme activity of each concentration was expressed as a percent of that determined in the absence of each compound. This then was transformed into a logit format, where logit=In (% activity/[100 - % activity]), and was plotted as a function of the log concentration of the compound. IC$_{50}$ values (i.e., logit=In (50/[100−50]=0) were determined only from correlation coefficients of less than −0.985, and when more than 50% inhibition was achieved from duplicate samples.

Each compound was analyzed between 4 and 8 occasions. A two-tailed student's t-test was performed to compare two means (see, Miller, *Simultaneous Statistical Inferences*, McGraw-Hill, New York, NY, page 76 (1966)). When more than two means were compared, one-way analysis of variance and the Bonferroni multiple t-test were used (see, Miller, *Simultaneous Statistical Inferences*, McGraw-Hill, New York, N.Y., page 76 (1966)). Statistical significance was taken at the level of $p<0.05$.

Table II below lists the important biological data for compounds according to the invention. The IC$_{50}$ values and the activity levels for AChE and BChE inhibition are listed as compared to the prior art standard compounds. The compound numbers Ex. 1-9 refer to the same compounds structures that were listed as compounds 1-9 in Table I, above.

TABLE II

| Compound Number | | AChE IC$_{50}$(nM) | BChE IC$_{50}$(nM) |
|---|---|---|---|
| (A) | (-)-physostigmine (comparative std.) | 27.9 ± 2.4 | 16.0 ± 2.9 |
| (B) | (-)-N(1)-Norphysostigmine (comparative std.) | 21.0 ± 1.0 | 2.0 ± 1.0 |
| (C) | (-)-physovenine (comparative std.) | 27.1 ± 0.8 | 2.7 ± 1.4 |
| Ex. 1 | | 13.5 ± 1.5 | 0.7 ± 0.1 |
| Ex. 2 | | 25.7 ± 2.8 | 6.8 ± 1.3 |
| Ex. 3 | | 27.2 ± 7.1 | 1657.1 ± 353.8 |
| Ex. 4 | | 29.0 ± 5.6 | 5278.8 ± 354.2 |
| Ex. 5 | | 30.1 ± 0.2 | 3429.5 ± 258.9 |
| Ex. 6 | | 25.5 ± 3.3 | 963.1 ± 106.4 |
| Ex. 7 | | >10,000 | 45.3 ± 12.4 |
| Ex. 8 | | 26.3 ± 3.8 | 1865.8 ± 291.4 |
| Ex. 9 | | 197.3 ± 34.1 | 22.5 ± 0.1 |

In Vivo Duration of Activity Studies

Catheters, filled with heparinized saline, were tied into the right femoral vein and artery of anesthetized male rats, which then were restrained in a plaster cast and allowed to recover from anesthesia in a temperature-controlled enclosure. Plasma samples were withdrawn to quantitate untreated levels of AChE activity. At 90 min after surgery, hexamethonium bromide (5 mg/kg, i.p.) was administered, followed by attopine methylbromide (4 mg/kg, s.c.) 10 min later. These quaternary nicotinic and muscarinic antagonists, do not enter brain and inhibit peripheral cholinergic overdrive associated with cholinesterase inhibition, which may be deleterious to the animal. Two hours after surgery, either (i) physostigmine, (ii) physostigmine derivatives, or (iii) THA was administered i.v. Plasma samples were removed at intervals between 2 min and 8 hour, intmediately frozen to −70° C. and then assayed for cholinesterase inhibition. AChE inhibition was measured as described above, with necessary mcdifications required for quantitation from rat plasma.

All drugs were formulated in a manner consistent with i.v. administration. Specifically, drugs were dissolved in Tween 80/EtOH (3:1, V:V), approximately 100 νl and then were diluted in excess of 1:9 (V:V) with isotonic saline. The use of Tween 80/EtOH did not affect either AChE or BChE inhibitory activity of compounds in in vitro studies (Yu et al., Helv. Chim. Acta 74, pages 761-766, (1991)). Doses were determined in prior studies involving the measurement of rectal temperature and tremor; two centrally-mediated actions of cholinesterase inhibitors and cholinergic agonists.

FIG. 1 demonstrates the in vivo inhibition of the enzyme acetylcholinesterase (AChE), i.e., the activity of cholinesterase inhibitiors such as (−)-physostigmine and (−)-thiaphysovenine possess good inhibition properties (as predicted from in vitro studies), but their duration of action is short. Compared to THA (tactine); THA inhibition is achieved only at a high dose (close to toxicity), but is of longer duration.

Figure 2:
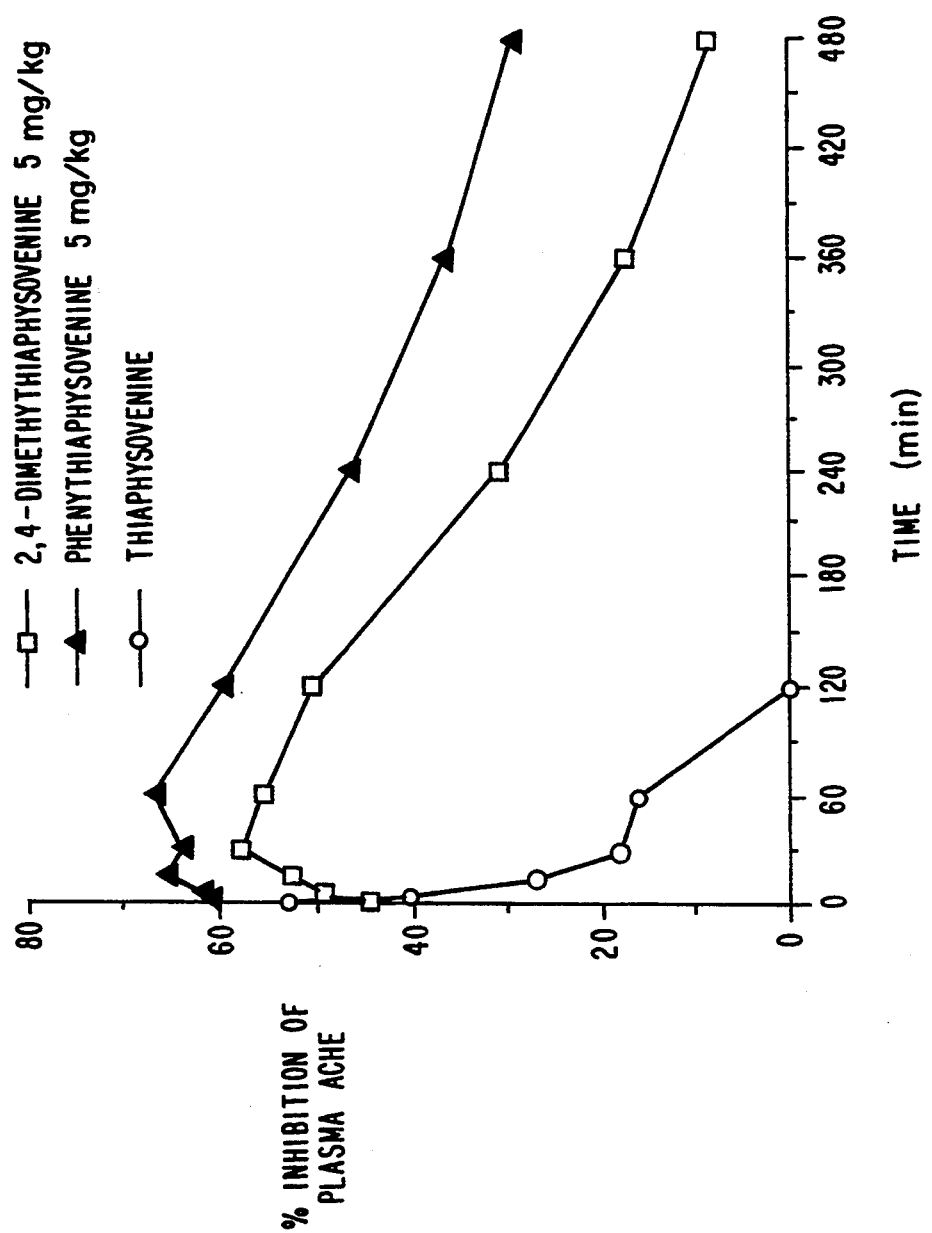
FIG. 2 compares the in vivo inhibition rates and duration of activity for thiaphysovenine and thiaphysovenol phenylcarbamates in inhibiting AChE.

FIG. 2 shows AChE inhibition by I.V. (−)-thiaphysovenine, (−)-Phenyl- and (−)-2',4'-dimethylphenyl-thiaphysovenine in rat plasma. The activity and persistence of 5 mg/kg doses of the tested compounds were compared for a 480 minute period. FIG. 2 shows that whereas (−)-thiaphysovenine has a short duration of action (also see FIG. 1), carbamates, i.e., phenylcarbamates, possess high inhibition of long duration. This is achieved at doses without side-effects or toxicity. Such results are surprising and provide potent new in vivo AChE inhibitors.

Another unexpected and surprising discovery was made for the dimethylcarbamate of (−)-thiaphysovenol ((−)-3, 3a, 8, 8a-Tetrahydro-3a, 8-dimethyl-2H-thieno[2,3b]indole-5-ol dimethylcarbamate. Surprisingly, the dialkylcarbamate possesses longlasting inhibiting properties. The mono-substituted carbamate (thiaphysovenine) has good inhibition properties but does not persist.

The foregoing description of the specific embodiments will so fully reveal the general nature of the invention that others can, by applying current knowledge, readily modify and/or adapt for various applications such specific embodiments without departing from the generic concept and therefore such adaptations are intended to be comprehended within the meaning and range of equivalents of the disclosed embodiments. It is to be understood that the phraseology or terminology employed herein is for the purpose of description only and not of limitation.

We claim:

1. A compound of the formula

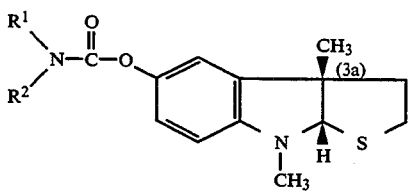

wherein $R^1$ is H or a linear or branched chain $C_1$-$C_{10}$ alkyl group; and $R^2$ is selected from the group consisting of a linear or branched chain —$C_1$-$C_{10}$ alkyl group, or

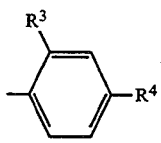

wherein $R^3$ and $R^4$ are independently selected from the group consisting of H and a linear or branched chain $C_1$-$C_{10}$ - alkyl group;

and with the proviso that when one of $R^1$ or $R^2$ is a H or a methyl group, the other of $R^1$ or $R^2$ is not H; including optical isomers of the 3aS series.

2. A compound according to claim 1, wherein
$R^1$ is H and $R^2$ is $C_4$-$C_{10}$ alkyl;
$R^1$ and $R^2$ are independently $C_1$-$C_{10}$ alkyl; or
$R^1$ is H and $R^2$ is a group of the formula

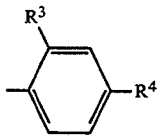

wherein
$R^3$ and $R^4$ are both H or a —$CH_3$ group;
$R^3$ is selected from the group consisting of a methyl, ethyl, or isopropyl group and $R^4$ is H; or
$R^3$ is H and $R^4$ is an isopropyl group.

3. A racemic compound according to the formula

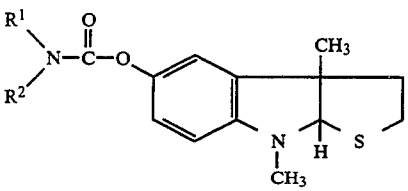

wherein $R^1$ is H or a linear or branched chain $C_1$-$C_{10}$ alkyl group; and $R^2$ is selected from the group consisting of
a linear or branched chain —$C_1$-$C_{10}$ alkyl group, or

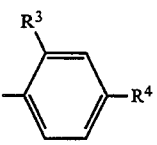

wherein $R^3$ and $R^4$ are independently selected from the group consisting of H and a linear or branched chain $C_1$-$C_{10}$ - alkyl group;

and with the proviso that when one of $R^1$ or $R^2$ is a H or a methyl group, the other of $R^1$ or $R^2$ is not H; including optical isomers.

4. A racemic compound according to claim 3, wherein
$R^1$ is H and $R^2$ is $C_4$-$C_{10}$ alkyl;
$R^1$ and $R^2$ are independently $C_1$-$C_{10}$ alkyl; or
$R^1$ is H and $R^2$ is a group of the formula

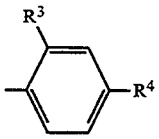

wherein
$R^3$ and $R^4$ are both H or a —$CH_3$ group;
$R^3$ is selected from the group consisting of a methyl, ethyl, or isopropyl group and $R^4$ is H; or
$R^3$ is H and $R^4$ is an isopropyl group.

5. A compound according to claim 1, wherein $R^3$ is independently selected from the group consisting of H, —$CH_3$, —$CH_2$—$CH_3$, and —$CH(—CH_3)_2$, and $R^4$ is independently selected from the group consisting of H, —$CH_3$, and —$CH(—CH_3)_2$.

6. A pharmaceutical composition comprising a pharmaceutically effective amount of a compound according to claim 1 and a carrier.

7. A method for treating cholinergic disorders comprising administration of an effective amount of a compound according to claim 1 to a mammal in need of such treatment.

8. A method according to claim 7, wherein the cholinergic disorder is selected from the group consisting of glaucoma, Myasthenia Gravis, Alzheimer's disease.

9. A method for inhibiting acetylcholinesterase activity comprising administering an effective amount of a compound according to claim 1 to a mammal in need thereof.

10. A method for inhibiting acetylcholinesterase activity comprising transdermally administering an effective amount of a compound according to claim 1 to a mammal in need thereof.

11. A method for inhibiting butyrylcholinesterase activity comprising administering an effective amount of a compound according to claim 1 in a mammal.

12. A method for treating organophosphate poisoning in a mammal comprising administering an effective amount of a compound according to claim 1.

13. A compound according to claim 1, wherein $R^1$ is H and $R^2$ is $C_4$-$C_{10}$ alkyl;

$R^1$ and $R^2$ are independently —$CH_3$;

or $R^1$ is H and $R^2$ is a group of the formula

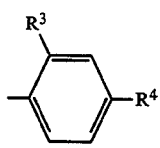

wherein $R^3$ and $R^4$ are both H or a —$CH_3$ group;

$R^3$ is selected from the group consisting of a methyl, ethyl, or isopropyl group and $R^4$ is H;

or $R^3$ is H and $R^4$ is an isopropyl group.

14. A racemic compound according to claim 3, wherein $R^1$ is H and R is $C_4$-$C_{10}$ alkyl;

$R^1$ and $R^2$ are independently —$CH_3$; or $R^1$ is H and $R^2$ is a group of the formula

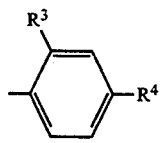

wherein $R^3$ and $R^4$ are both H or a —$CH_3$ group;

$R^3$ is selected from the group consisting of a methyl, ethyl, or isopropyl group and $R^4$ is H;

or $R^3$ is H and $R^4$ is an isopropyl group.

* * * * *

UNITED STATES PATENT AND TRADEMARK OFFICE
CERTIFICATE OF CORRECTION

PATENT NO. : 5,378,723
DATED : January 3, 1995
INVENTOR(S) : Brossi et al.

It is certified that error appears in the above-indentified patent and that said Letters Patent is hereby corrected as shown below:

Column 2, line 32, after "of" insert --a linear or branched chain $-C_1-C_{10}$ group or

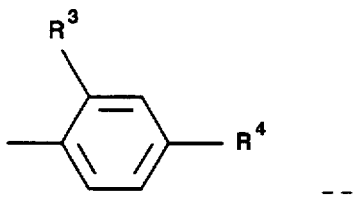

--

Column 2, line 44, change "Tactine" to --Tacrine--

Signed and Sealed this

Sixteenth Day of May, 1995

*Attest:*

BRUCE LEHMAN

*Attesting Officer*  *Commissioner of Patents and Trademarks*